US011594328B2

(12) United States Patent
Agarwal et al.

(10) Patent No.: US 11,594,328 B2
(45) Date of Patent: Feb. 28, 2023

(54) SYSTEMS AND METHODS FOR SEVA: SENIOR'S VIRTUAL ASSISTANT

(71) Applicants: Nimit Agarwal, Phoenix, AZ (US); Salim Hariri, Tucson, AZ (US); Sumit Agarwal, Phoenix, AZ (US)

(72) Inventors: Nimit Agarwal, Phoenix, AZ (US); Salim Hariri, Tucson, AZ (US); Sumit Agarwal, Phoenix, AZ (US)

(73) Assignee: Arizona Board of Regents on Behalf of the University of Arizona, Tucson, AZ (US)

(*) Notice: Subject to any disclaimer, the term of this patent is extended or adjusted under 35 U.S.C. 154(b) by 256 days.

(21) Appl. No.: 16/554,069

(22) Filed: Aug. 28, 2019

(65) Prior Publication Data

US 2020/0075160 A1  Mar. 5, 2020

Related U.S. Application Data (60) Provisional application No. 62/723,799, filed on Aug. 28, 2018.

(51) Int. Cl.
*G16H 40/67* (2018.01)
*G06F 9/451* (2018.01)
*G16H 50/30* (2018.01)
*G16H 10/60* (2018.01)

(52) U.S. Cl.
CPC ............. *G16H 40/67* (2018.01); *G06F 9/451* (2018.02); *G16H 10/60* (2018.01); *G16H 50/30* (2018.01)

(58) Field of Classification Search
CPC ........ G16H 40/67; G16H 10/60; G16H 50/30; G06F 9/451
USPC ......................................................... 705/2-3
See application file for complete search history.

(56) References Cited

U.S. PATENT DOCUMENTS

| | | | |
|---|---|---|---|
| 6,283,761 B1* | 9/2001 | Joao ....................... | G06Q 40/08 434/236 |
| 2016/0296159 A1* | 10/2016 | Larson ............... | A61B 5/02055 |
| 2017/0004260 A1* | 1/2017 | Moturu ................. | G16H 50/20 |
| 2017/0027498 A1* | 2/2017 | Larson .................. | A61B 5/002 |
| 2018/0025133 A1* | 1/2018 | Opler ..................... | G16H 50/20 705/2 |
| 2019/0104982 A1* | 4/2019 | Dunn ....................... | A61B 5/00 |
| 2019/0180871 A1* | 6/2019 | Doerflinger ............ | G16H 50/20 |
| 2020/0261013 A1* | 8/2020 | Ben-Oren .............. | G16H 20/70 |

OTHER PUBLICATIONS

Hariri et al., "Digitial Patient Assistant (DPA): Architecture and Deployment," Digital Patent Assistant Project, Jun. 12, 2018.

* cited by examiner

*Primary Examiner* — Michael Tomaszewski
(74) *Attorney, Agent, or Firm* — Blank Rome LLP (57) ABSTRACT

Systems and methods for computer-implemented patient assistance are disclosed. In certain embodiments, the invention contemplates receiving patient data from plurality of sensors at a patient computer, transmitting patient data to a server, monitoring and analyzing the patient data at the server, and outputting recommended actions from the server to a personnel computer. The recommended actions are calculated based on safety considerations, emotional considerations, and/or a patient's treatment plan.

20 Claims, 8 Drawing Sheets

SYSTEMS AND METHODS FOR SEVA: SENIOR'S VIRTUAL ASSISTANT

CROSS-REFERENCE TO RELATED APPLICATIONS

This application claims the benefit of U.S. Provisional App. No. 62/723,799, filed Aug. 28, 2018, the entire contents of which are hereby incorporated by reference.

FIELD OF THE INVENTION

The present invention relates to systems and methods for computer-implemented digital patient assistance in care facilities.

BACKGROUND OF THE INVENTION

The use of advanced IoT (Internet of Things) devices and medical sensors have had a positive impact on patient care, and shows continuing promise in decreasing preventable injuries, improving healthcare quality, and reducing costs. Such technology allows continuous virtual monitoring and bi-directional virtual communication between the patients and healthcare staff, therefore offering the capabilities of remote diagnosis, treatments and the ability to take proactive actions to prevent injuries and mitigate major, potentially fatal health incidents such as cardiac events, delirium, and falls.

To develop remote monitoring, diagnosis and injury prevention capabilities for patients in hospitals and other healthcare centers, innovative architecture is needed that can effectively utilize the advancements in IoT, wearable sensor technologies, autonomic and cloud computing. The IoT can be viewed as a ubiquitous network that enables monitoring the patient's room and patient's mobility in a HIPAA compliant manner, while respecting patient privacy by collecting and processing de-identified data generated by the deployed sensors. Cloud and autonomic computing will be used to deliver the required innovative AI healthcare services for improving the quality of care.

Sensor medical technologies are important for their impacts on improving the health and treatment of patients, especially in hospitals, rehab centers, home health care, senior living, assisted living, etc. The use of advanced IoT (Internet of Things) devices and medical sensors by patients, promises to decrease preventable injuries, improve the quality of healthcare and reduce costs. Such technology will allow patients to communicate/ alert the healthcare staff about their current situation, if at risk. It will also allow nurses and physicians to continuously monitor patient's health, offering the capabilities of remote diagnosis, treatments and to take proactive actions to prevent injuries and mitigate major health incidents (Cardiac events, delirium, falls, pressure injuries, etc.).

To develop remote monitoring, diagnosis and injury prevention capabilities for patients in hospitals and other healthcare centers, innovative architecture is needed that can effectively utilize the advancements in IoT, wearable sensor technologies, autonomic and cloud computing. The IoT can be viewed as a ubiquitous network that enables monitoring the patient's rooms and patient's mobility in a discrete HIPAA compliant manner, while respecting patient privacy by collecting and processing the deidentified data generated by the deployed sensors. Cloud and autonomic computing will be used to deliver the required innovative AI healthcare services for improving the quality of care.

The Senior's Virtual Assistant ("SeVA") aims to provide these, but to add robustness and meaning to the information and experience provided by using artificial intelligence that is capable of emotional learning and sentiment analysis— technology that has demonstrated value in the fields of consumer and political analytics, and by its processes, also guards against potential programmer/creator bias that may limit its longevity of function.

The technical challenge lies in making this user-friendly to a point that it can be used interactively by patients with limited smartphone technology skills especially older adults. The other challenge is to be able to use this technology in a patient with delirium or altered mentation and be capable of obtaining and conveying adequate meaningful information to clinical teams in order to make timely therapeutic decisions. The simulation scenarios to create this technology will be unique and innumerable, which will constantly need to be updated to meet demands of the healthcare system.

In a manuscript written by Dr. Inouye, a major researcher on Delirium Care, published by Lancet Mar. 8, 2014 edition, supported in part by Grant No. P01AG031720 from the National Institute on Aging: "Delirium affects up to 50% of hospitalized patients, and costs over \$164 billion (2011) per year in the United States and over \$182 billion (2011) per year in 18 European countries combined. As a preventable condition in 30-40% of cases, delirium holds substantial public health relevance as a target for interventions to prevent its associated burden of downstream complications and costs. Accordingly, delirium is now included on the patient safety agenda, and has been increasingly targeted as an indicator of healthcare quality for seniors."

The present mainstay of therapy for delirium is prevention, early recognition and non-pharmacological management. Currently, there are no specialized technology-based interactive devices to our knowledge that are focused on this task, much less capitalizes and utilizes artificial intelligence that emulates emotional intelligence, and not just basic-level pattern recognition and learning. The SeVA aims to have a more clinically meaningful, seamless therapeutic experience because of this.

SUMMARY OF THE INVENTION

The SeVA platform described herein is a user-level intuitive medical device akin to Alexa or Siri, which can interact with the patient and medical teams in an Acute Inpatient, Subacute and Ambulatory Care setting in order to respond to care issues, including falls prevention and recognition of medical complications, especially in patients with physical and cognitive impairment secondary to acute illness and delirium, dementia and other neuro-cognitive illnesses.

The goal for the SeVA is to achieve a real-time understanding of patients with dementia or delirium, their medical needs, stress, emotion and cognition, so that it can converse with the patient as if they have a 24/7 companion. For example, SeVA can auto activate daily to ask the patient to spell "LUNCH" backwards, (part of Delirium Triage Screen) a standard test to detect delirium. If the answer is incorrect, a series of other questions will be asked, and the nurse informed about the possibility of delirium in the patient, so that management can be started earlier.

Constant cognitive interaction can be provided with desired music, latest news, utilization of spiritual and meditative techniques, which can be programmed through the SeVA system using autonomic computing based on a patient's mood, hence giving some respite to the caregiver. SeVA can also be set to be voice enabled at specific times of the day to vocally ask the patient about bathroom needs every 2 hours, hence, optimizing the timely nursing checks in the hospital setting. With further development and upgrades, SeVA will document this encounter in the patient's Electronic Health Record (EHR), thus decreasing nursing charting time and accurately recording patient events.

The proposed method and computerized system invention that we refer to as SeVA platform provides the following capabilities:

(1) A novel machine learning based scoring method called CARE (Cognition, Alertness, Restfulness, and Emotion) Scale for the diagnosis of early signs of delirium, and monitor changes in cognition, mood and emotion;

(2) A Socially Assistive Robot (SAR) for the monitoring of the CARE parameters that can facilitate decision making by caregivers and medical personnel to mitigate complications of delirium, cognitive decline, and prevent apathy;

(3) Use emerging sensor/wearable technology and advanced data analytics that integrate data from multiple sources and devices to significantly enhance the sensitivity and specificity of the SeVA platform for the detection of delirium and other cognitive impairment, as well as patient's current physical position and responses;

(4) The intelligent SAR provides the following unprecedented options for customization:
  Personalized prompts for patients to allow for visual reminders, medical and communication aids
  Programmable by caregivers to suit individual needs
  Companionship and psychosocial support in the form of personalized entertainment and other information delivery tailored to individual patients
  Workload support to nursing staff by performing periodic routine status checks on the patient and provide meaningful actionable items related to patient care. This will be scalable and customized to the required level of care including hospitals, rehabilitation facilities, skilled nursing facilities, assisted living as well as home environments Low cost mmWave radar system that will predict movement and behaviors that can result in a fall without compromising patient privacy. The radar system uses motion instead of visual imaging, which decreases risk of privacy concerns as no facial or bodily features are recognized by radar imagery. It detects change in position of patient as compared to currently used pressure-based sensors, which have a high false alarm rate.

In certain embodiments, the invention contemplates receiving patient data from a plurality of sensors at a patient computer, transmitting patient data to a server, monitoring and analyzing the patient data at the server, and outputting recommended actions from the server to a personnel computer. The recommended actions are calculated based on safety considerations, emotional considerations, and/or a patient's treatment plan.

In other embodiments, the plurality of sensors used by the invention are one or more of a motion detector, a tv/music entertainment sensor, a smart body sensor, an emotion/stress sensor(s), and a temperature sensor.

In yet other embodiments, the patient computer communicates with the centralized server running the SeVA Management Services modules through a portal.

In yet other embodiments, the system stores patient data in a protected database, that is HIPAA compliant.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose. Several preferred embodiments of the invention are described for illustrative purposes; it being understood that the invention may be embodied in other forms not specifically shown in the drawings.

As will be explained in greater detail herein, a goal for the present invention is to:

(1) Continuously collect data from sensor and smart devices;

(2) Analyze this data using machine learning and AI techniques with the goal of detecting the early signs of cognitive impairment/delirium;

(3) Predict possible poor outcomes/complications related to delirium;

(4) Alert the medical teams about delirium and initiate early intervention;

(5) Improve the delivery of non-pharmacological interventions;

(6) Improve the cognition of the patient;

(7) Improve caregiver burden and workflow of the medical and nursing teams;

(8) Prevent complications in the hospital including falls, aspiration risk leading to pneumonia; and (9) Decrease morbidity and mortality related to delirium.

Figure 1:
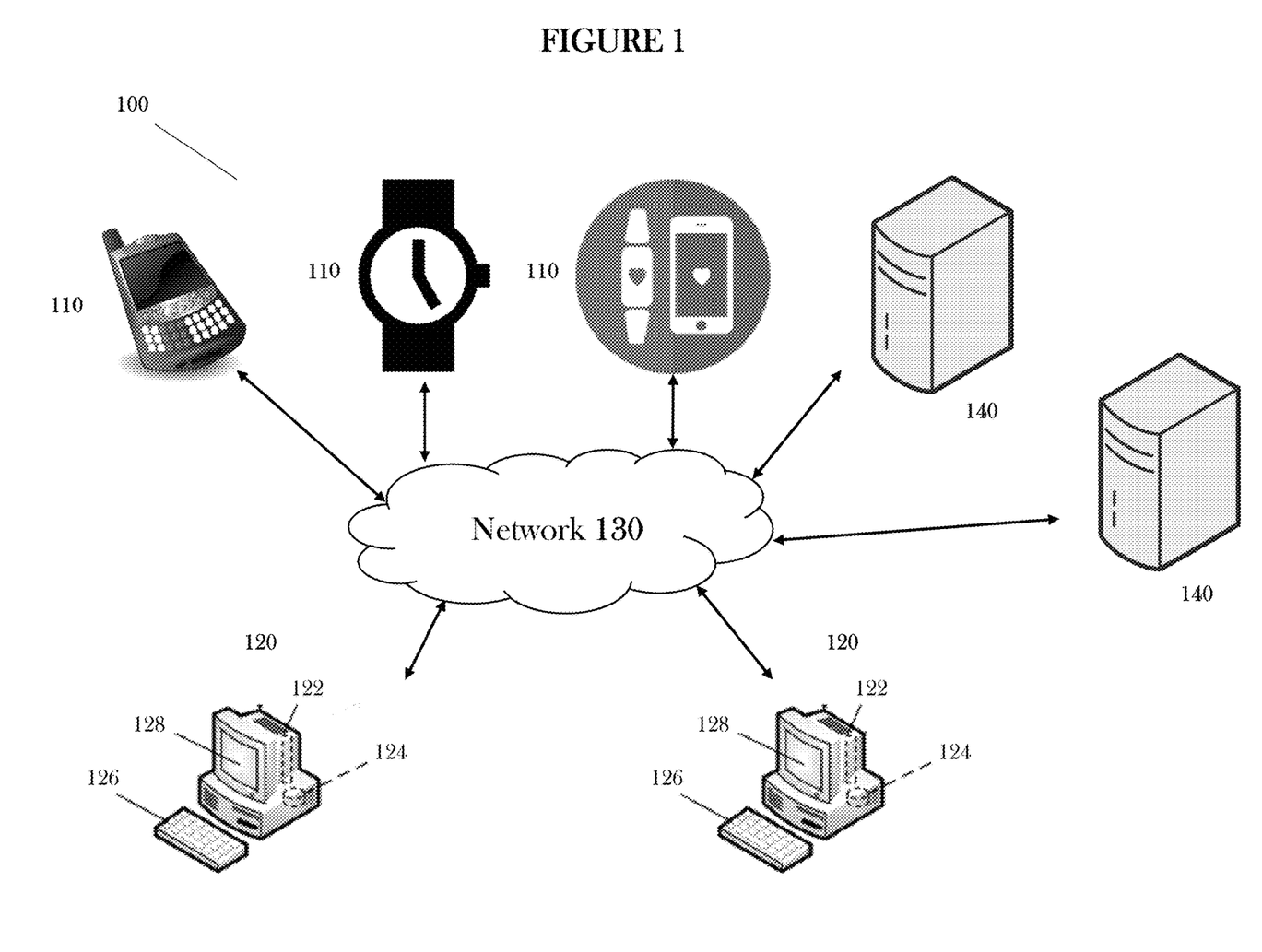
FIG. 1 is a diagram of the hardware and network of the system, in accordance with an exemplary embodiment.

FIG. 1 is an exemplary embodiment of the SeVA system 100. In the exemplary system 100, one or more peripheral devices 110 are connected to one or more computers 120 through a network 130. Examples of peripheral devices 110 include clocks, smartphones, smart-clocks, tablets, wearable devices such as smartwatches, medical devices such as EKG and blood pressure monitors, and any other devices that collect patient data that are known in the art. The network 130 may be a wide-area network, like the Internet, or a local area network, like an intranet. Because of the network 130, the physical location of the peripheral devices 110 and the computers 120 has no effect on the functionality of the hardware and software of the invention. Both implementations are described herein, and unless specified, it is contemplated that the peripheral devices 110 and the computers 120 may be in the same or in different physical locations. Communication between the hardware of the system may be accomplished in numerous known ways, for example using network connectivity components such as a modem, wireless adapter, or Ethernet adapter. The peripheral devices 110 and the computers 120 will both include or be attached to communication equipment. Communications are contemplated as occurring through industry-standard protocols such as HTTP.

Each computer 120 is comprised of a central processing unit 122, a storage medium 124, a user-input device 126, and a display 128. Examples of computers that may be used are: commercially available personal computers, open source computing devices (e.g. Raspberry Pi), commercially available servers, and commercially available portable device (e.g. smartphones, smartwatches, tablets). In one embodiment, each of the peripheral devices 110 and each of the computers 120 of the system may have the digital patient assistance software related to the system installed on it. In such an embodiment, patient data may be stored locally on the networked computers 120 or alternately, on one or more remote servers 140 that are accessible to any of the networked computers 120 through the network 130. In alternate embodiments, the digital patient assistance software runs as an application on the peripheral devices 110.

Figure 2:
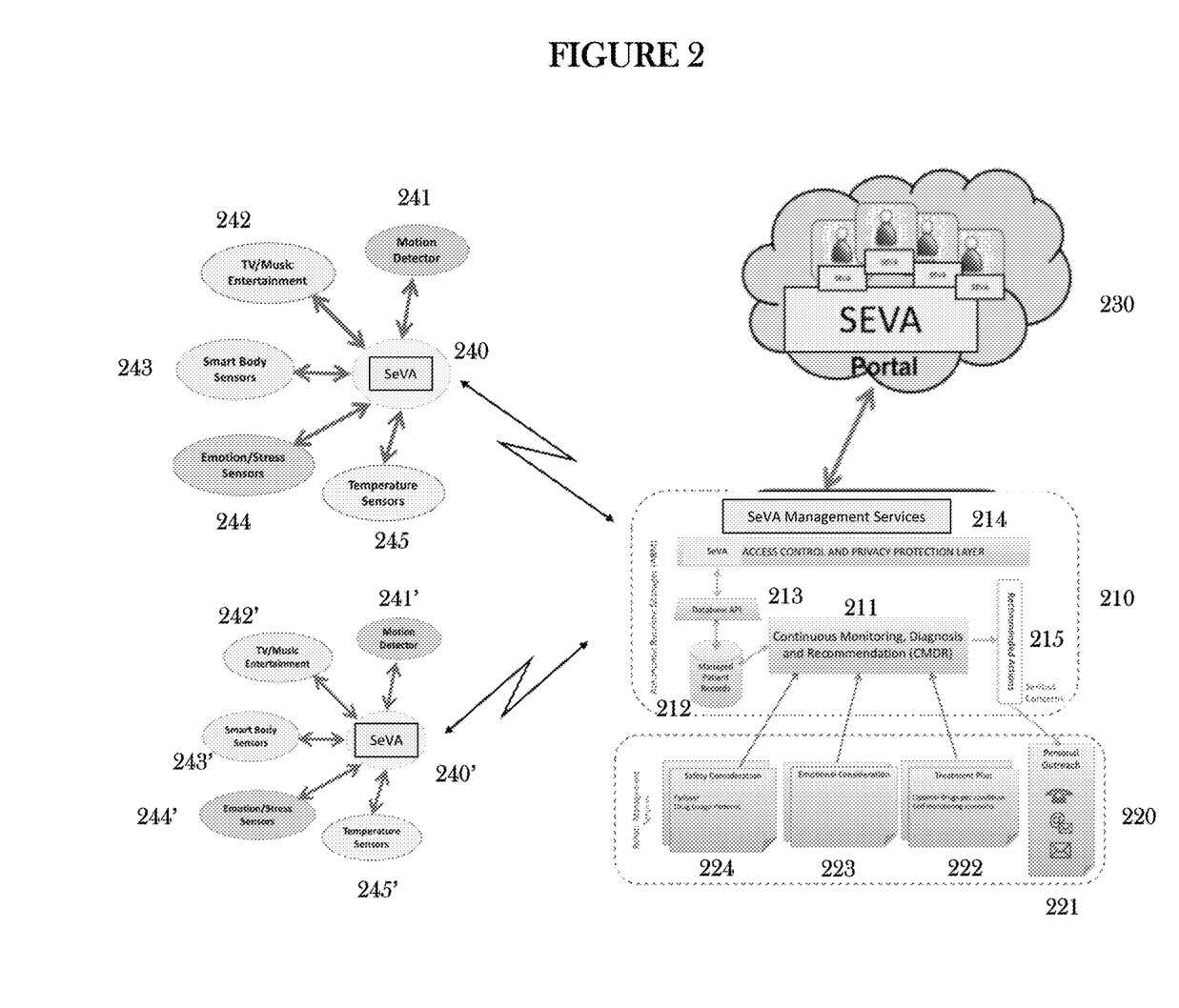
FIG. 2 is a diagram of the main software components used in the implementation of the system and how they interact, in accordance with an exemplary embodiment.

FIG. 2 is a diagram of the main components used in the implementation of the digital patient assistance system, in accordance with an exemplary embodiment of the invention.

As shown in FIG. 2, the main system components include SeVA Management Services 210, which are comprised of software modules. The Continuous Monitoring, Diagnosis, and Recommendation module 211 performs management protocols including monitoring patients, diagnosing patients, and issuing recommendations to staff. The Managed Patient Records 212 are stored in a database. The Database API 213 acts as a liaison between the Managed Patient Records 212 and SeVA Access Control and Privacy Protection Layer 214, which protects the patient records, in compliance with HIPAA standards. The Continuous Monitoring, Diagnosis, and Recommendation module 211 outputs Recommended Actions 215 based on the data it analyzes. Recommended actions include, but are not limited to the detection of delirium, falls, changes in position, cardiac arrhythmias, etc.

The SeVA Management Services software 210 connects to Rehab Management Services 220, which is comprised of a number of modules. The Personal Outreach module 221 is responsible for contacting personnel of interest by phone, email, or other electronic means to advise of patient's status and Recommended Actions 215. Other modules such as Treatment Plan 222, Emotional Consideration 223, and Safety Consideration 224 connect to the Continuous Monitoring, Diagnosis, and Recommendation module 211, acting to tailor the Recommended Actions 215. Recommended Actions may be tailored based on patient's risks as determined by medical staff, patient preferences as determined by patient or caregiver.

SeVA Management Services 210 also connects to the SeVA Portal 230, which mediates communication and data transfer between SeVA Management Services 210 and one or more SeVAs 240, 240'. Each SeVA 240, 240' is comprised of sensor arrays associated with the patient being monitored. Those sensors include motion detectors 241, 241', tv/music entertainment 242, 242', smart body sensors 243, 243', emotion/stress sensors 244, 244', and temperature sensors 245, 245'. Other sensors that may occur to one of ordinary skill in the art are also within the scope of the invention.

The SeVA Management Service 210 will be utilized for patient care in the following categories, but not limited to: (1) Recognize medical emergencies; (2) Assist clinical nursing teams with 1 hourly rounding checks to determine patient needs; (3) To assess emotional and personal needs connected to medical care including pain assessment; (4) To assess and monitor vitals including Heart Rate, breathing patterns, temperatures; (5) Recognize and prevent falls in high risk patients; (6) Improve the care of cognitively impaired patients suffering with delirium and dementia; and (7) Cater to the personal preferences and choices of the patients in music, relaxing techniques to improve patient experience.

Some exemplary scenarios to explain the utility of the SeVA in the healthcare setting are:

(1) Recognize medical emergencies—(a) Recognition of seizures; (b) Recognition of choking/aspiration; and (c) Recognition of abnormal heart rhythms.

With the use of the sensor (mm Wave radar system), gestures can be detected which replicate seizure activity, hand waiving asking for help and other activities like getting out of bed. These gestures will be communicated to the SeVA, and immediately the nursing station will be alerted for intervention. For choking/aspiration, using voice recognition, bodily motion and breathing pattern, the sensor can detect if the patient is aspirating/choking and through the SeVA, alert the healthcare staff for intervention.

In most Skilled Nursing Facilities, Inpatient Rehabilitation, non-telemetry medical/surgical floors, telemetry is an additional cost and a service that is unavailable. By using a heart monitor sensor, in conjunction with specialized technology called HRV (heart rate variability) we can detect asystole, ventricular fibrillation, tachycardia and bradycardia and alert the clinical staff about impending cardiac complications.

(2) Assist clinical nursing teams with timely rounding checks to determine patient needs:

In an acute healthcare setting, nursing teams assess a patient by rounding and going through a checklist of items to determine the patients' needs and safety. Examples are: (i) Checking if the nurse call light button is within reach; (ii) If the patient needs to use the bathroom; (iii) Access to water; (iv) Patient is in pain; (v) Needs repositioning; and (vi) Reorientation techniques in cognitively impaired patients.

With the SeVA, these scenarios can be automated, and alert the nursing staff for any needs, thereby improving the efficiency and timeliness of intervention.

(3) To assess emotional and personal needs connected to medical care including pain assessment:

The SeVA can incorporate the Faces scale for pain assessment and determine the patient's emotional/stress/pain state using our partner BPU Holdings technology (www.bpuholdings.com), AI emotional assistant, and thereby improve patient experience and timeliness of care. This can also help with improving the personal experience of the patient with the healthcare setting resulting in improved HCAHPS scores.

(4) To assess and monitor vitals including Heart Rate (HR), breathing patterns, temperatures:

Heart Rate Variability (HRV) will be monitored using smart watch.

Cater to the personal preferences and choices of the patients in music, relaxing techniques to improve patient experience. For breathing patterns and temperature monitoring, we will incorporate BPU Holding's technology.

(5) Recognize and prevent falls in high risk patients:

The current technology for preventing and recognizing falls is through pressure based mechanical devices attached to the patient's bed, which do not connect/communicate to the nursing station. These alarms have to be activated manually by the nurse, and when the alarm fires, the alarm location has to be manually located. This delays the timely intervention required to prevent adverse events like falls and has a high fall detection error rate. With the mmWave radar technology in SeVA, we can identify patient movements predisposing to falls, and alert the nursing staff for timely intervention.

(6) Improve the care of cognitively impaired patients suffering with delirium and dementia:

The prevalence of delirium in the hospital setting can be as high as 30%. Patients with hospital-induced delirium have a higher rate of complications, length of stay and cost of care. Delirium can be mitigated using non-pharmacological techniques by interacting with the patient using smart Artificial Intelligence, emotional assistant. This is a personal chat assistant, which can continuously interact with the patient in a personalized/customized voice of preference, with the goal of orienting the patient to day-to-day activities including the latest news, sports, community/ personal cultural activities. These can be customized to the patient's preferences. Currently, this is very difficult to achieve because it requires a family member/companion to be continuously available with the patient.

(7) Cater to the personal preferences and choices of the patients in music, relaxing techniques to improve patient experience:

Non-pharmacological techniques like music therapy, light therapy, aromatherapy, and temperature can improve sleep wake patterns and decrease stress level, which will help with improving general patient experience and convalescence. Improved personal experience with healthcare setting directly correlates with improved HCAHPS scores leading to better reimbursement for hospital services through payors. These actions can leverage existing technologies like Amazon Alexa technology, IBM Watson, and other capabilities to be developed specifically to this project.

Figure 3:
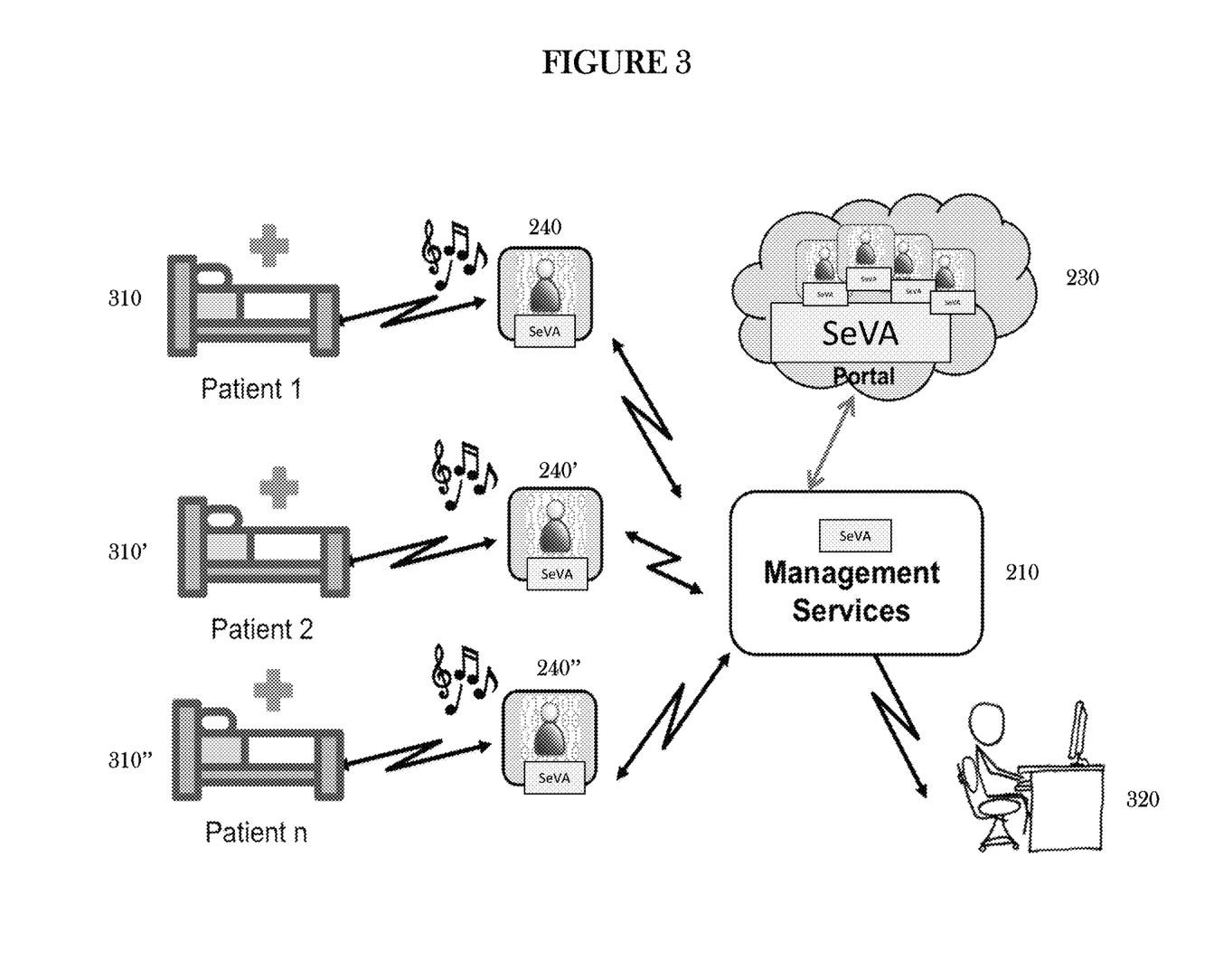
FIG. 3 is a diagram of an exemplary deployment of the system.

FIG. 3 shows an exemplary implementation of the systems and methods described herein, specifically in a Inpatient Rehabilitation Center or a medical center. In FIG. 3, one or more patients 310, 310', 310" are connected to one or more SeVAs 240, 240', 240". Those SeVAs 240, 240', 240" communicate with SeVA Management Services 210 through the SeVA Portal 230. The SeVA Management Services 210 analyzes patient data and output recommendations to interested personnel 320. Those recommended actions relate to assisting the personnel in attending to the needs of the patient.

Figure 4:
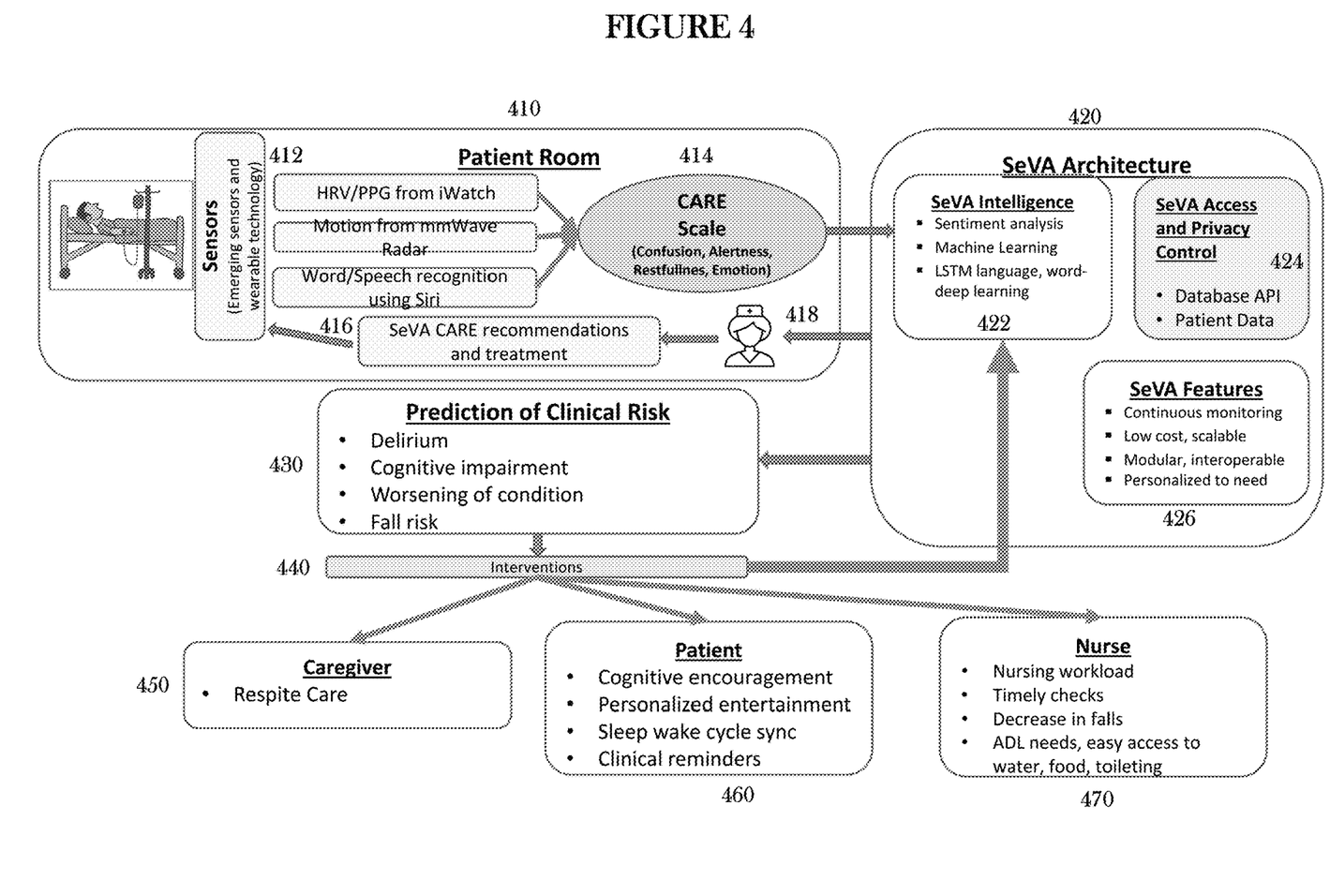
FIG. 4 is a diagram of another exemplary deployment of the system.

FIG. 4 is a diagram of another exemplary deployment of the system, as it would be deployed in a hospital. The patient, situated in a patient room 410, is coupled to one or more sensors 412, which are a combination of wearable technologies and emerging sensors such as temperature sensors, motion detector, a tv/music entertainment sensor, a smart body sensor, an emotion/stress sensor(s), as well as other medically oriented sensors (e.g. (HRV), photoplethysmograms (PPGs)). The sensor data is compiled by the system to determine a CARE scale 414 for the patient. The CARE scale is an analysis of the confusion, alertness, restfulness, and emotion of the patient.

The CARE scale 414 data, as well as any patient data the system is configured to accept, is transmitted to the logic architecture of the system, the SeVA architecture 420. The SeVA architecture 420 is comprised of the SeVA Intelligence module 422, the SeVA Access and Privacy Control module 424, and the SeVA Features module 426. The CARE scale 414 data is analyzed in the SeVA Intelligence module 422, which performs a sentiment analysis, while also incorporating machine learning, LSTM language and word-deep learning algorithms, as explained with reference to FIG. 7 below.

Predicting CARE's Alertness Parameter Basedon HRV Data Streams

There are various ways to measure alertness in medical literature. One of the commonest ways to assess the level of alertness is using Richmond Agitation and Sedation Scale (RASS), which is commonly used in the Intensive Care Unit (ICU). RASS is also a component of CAM assessment for delirium specially to differentiate between a calm and alert state as compared to Hyperactive and Hypoactive state to differentiate the type of delirium. Outside the medical literature, there are other areas where alertness assessment is important especially in the domains of work and driving. Lack of alertness in driving could result in serious accidents and injuries (Qiong et al. 2006; Coetzer et al. 2009). Research focusing on these areas have made use of electroencephalogram (EEG), heart rate variability (HRV) and computer vision data to assess alertness level. There are also products that exist in the market that assess alertness using computer vision or EEG data (Liang et al. 2005; Oron-Gilad et al. 2008; Sommer et al. 2010]. In this invention, we use LSTM neurons to characterize patient's alertness level on a scale from 1 to 10. We utilize both voice and HRV data to measure patients' alertness level. For collecting HRV data, we will use non-invasive, easy to wear hardware such as a smartwatch to collect PPG data. Although using EKG data could let us extract higher quality HRV data from the patient, reasons for utilizing PPG over EKG are as follows: (1) Decrease use of "tethers", e.g. EKG leads, telemetry monitor which themselves can increase risk for delirium by making the patient uncomfortable; (2) Continuous EKG monitoring/ telemetry is not available in all healthcare settings; and (3) Decrease cost by using easily available technology on the market. For scoring patient's alertness level using voice, we will be using SeVA voice-enabled module to interact with the patient. The module will initiate conversation with patient periodically and ask questions, For example: "John, SeVA is here, how are you doing?" or "Can I help you with something?" SeVA will measure the time it takes for the patient to respond to the question. A fusion module will be used to predict the final CARE Alertness score of the patient from the LSTMs based on HRV and Voice data streams.

The SeVA Access and Privacy Control module 424 is comprised of a database API and operates to store patient data. The SeVA Access and Privacy Control module 424 is preferably HIPAA compliant and controls patient data access in accordance with those regulations. The SeVA features module 426 is comprised of such operational features as continuous patient monitoring, modularity and interoperability with standard hardware, and personalization features, for example those that determine what patient data is analyzed.

The SeVA architecture 420 outputs CARE recommendations and treatments 416 to a medical practitioner 418 that implements them with respect to the patient. The SeVA architecture 420 also uses the patient data to formulate a prediction of clinical risk 430 to the patient. The prediction of clinical risk 430 is comprised of the patient's delirium state, the patient's cognitive impairment, the worsening of the patient's condition, and the patient's fall risk.

The prediction of clinical risk 430 is used for intervention 440 in the patient. Intervention 440 involves transmitting the prediction of clinical risk 430 to a caregiver 450, a patient 460, and/or a nurse 470. The caregiver 450 may use the interventional data 440 to provide respite care. The patient 460 may use his own interventional data 440 to provide himself cognitive encouragement, provide personalized entertainment, synchronize his sleep-wake cycle, and to provide himself clinical reminders. The nurse 470 uses the interventional data 440 to manage nursing workload, perform timely patient checks, ensure a decrease in patient falls, manage Activities of Daily Living (ADL) needs like provide easy access to water, food, and toileting. The system is designed to be used at hospitals, inpatient rehab facilities, skilled nursing facilities, assisted living facilities, and at home.

Figure 5:
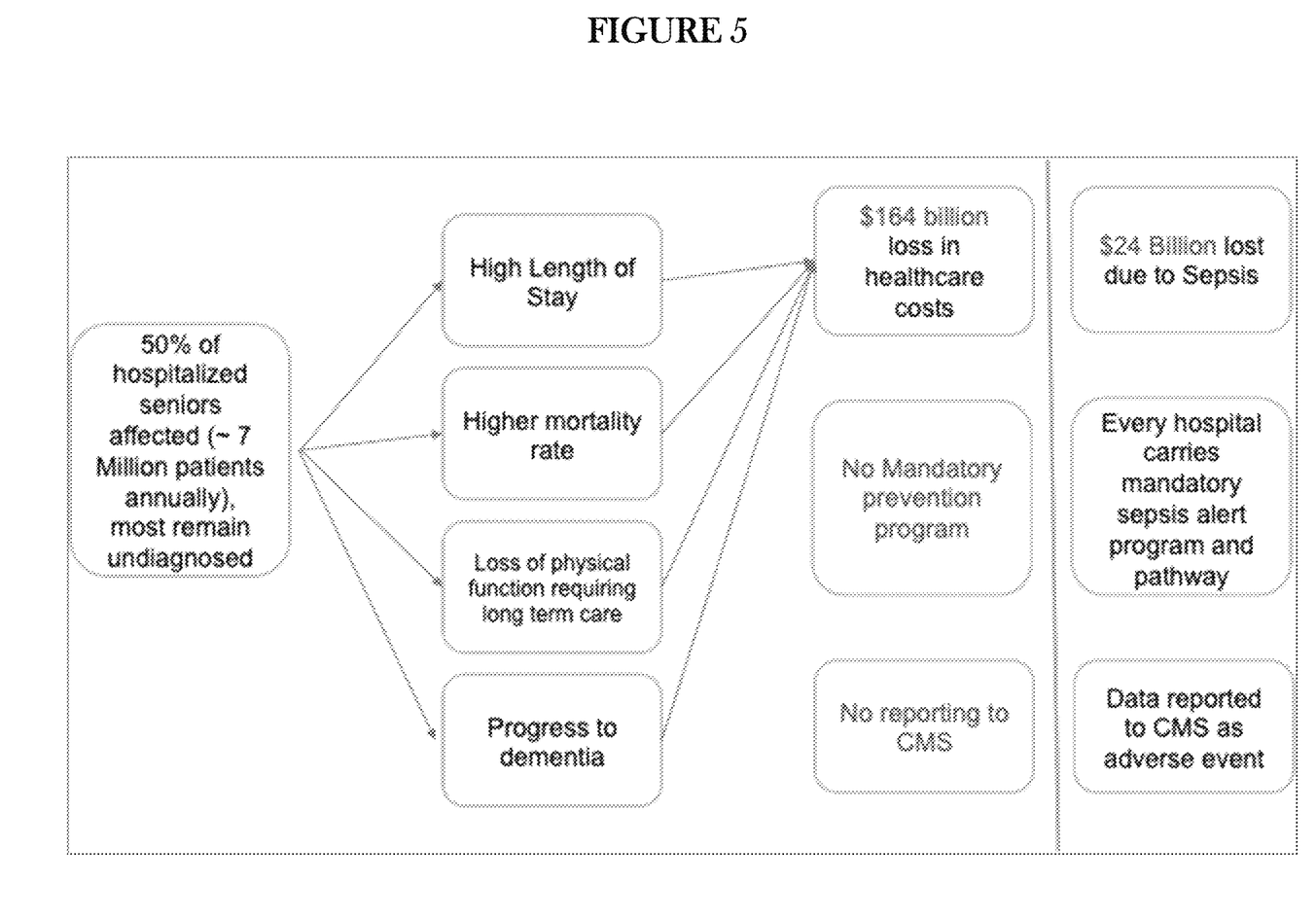
FIG. 5 is a diagram showing the lack of technology based systems related to delirium management that operate in hospitals and costs, mortality and morbidity associated with it.

FIG. 5 is a diagram showing the disadvantages of the present systems that operate in hospitals. At present, 50% of hospitalized older adults are affected by delirium (approximately 7 million patients) and most remain undiagnosed. That results in a high length of hospital stay, a higher mortality rate, a loss of patient physical function that requires long-term care, and a progress towards dementia. That inefficiency, a lack of patient monitoring, results in a $164 billion loss in healthcare costs related to delirium alone in 2014. Moreover, there is no mandatory prevention program and no reporting to Centers for Medicare and Medicaid Services (CMS). As compared to this, sepsis as a medical syndrome cost $24 billion to CMS in 2016, which led hospitals to implement mandatory sepsis alert programs and pathways.

Figure 6:
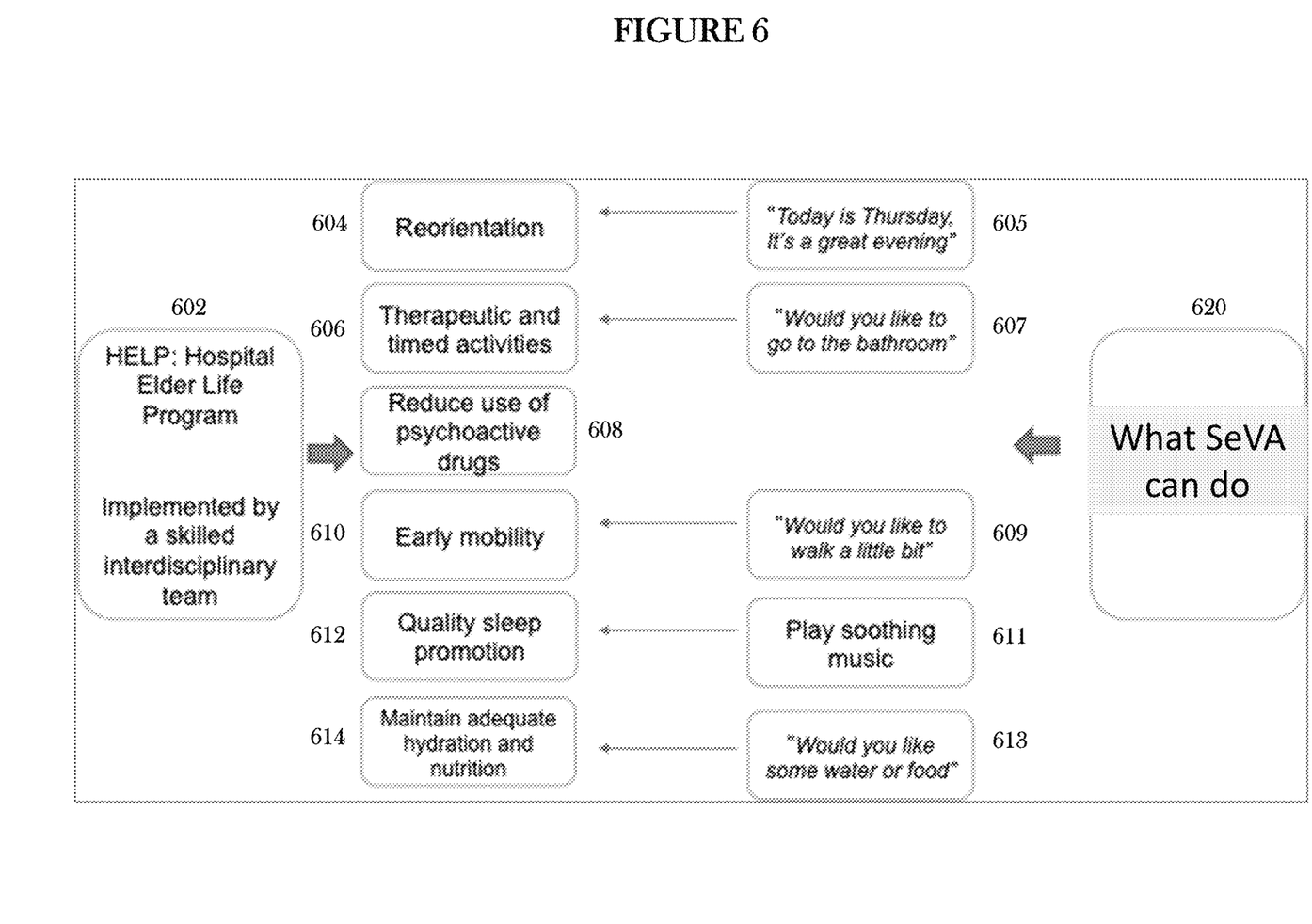
FIG. 6 is a diagram showing the exemplary functionalities that are available to the system comparing with current practices which are not technology based.

FIG. 6 is a diagram showing the exemplary functionalities that are available to the system. Specifically, the diagram shows how the system may be implemented similar to the Hospital Elder Life Program (HELP) 602, which is typically implemented by a skilled interdisciplinary team. The HELP 602 program includes several functionalities, as explained herein. Reorientation 604 involves orientating the patient to the environment. A sample statement a system may make to reorient a patient is "Today is Thursday. It's a great evening" 605. Therapeutic and Timed Activities 606 involves the system providing reminders for such activities. An example would be asking the patient, "Would you like to go to the bathroom?" 607. The system may also act to reduce the use of psychoactive drugs 608.

Other functionalities that the system may implement are encouraging Early Mobility 610, for example, asking the patient "Would you like to walk a bit?" 609. The system also provides Quality Sleep Promotion 612, for example, by Playing Soothing Music 611. The system also maintains the patient's adequate hydration and nutrition 614, for example, asking the patient, "Would you like some water or food?" 613. Together, all of the foregoing functionalities form the capabilities of the SeVA 620.

Figure 7:
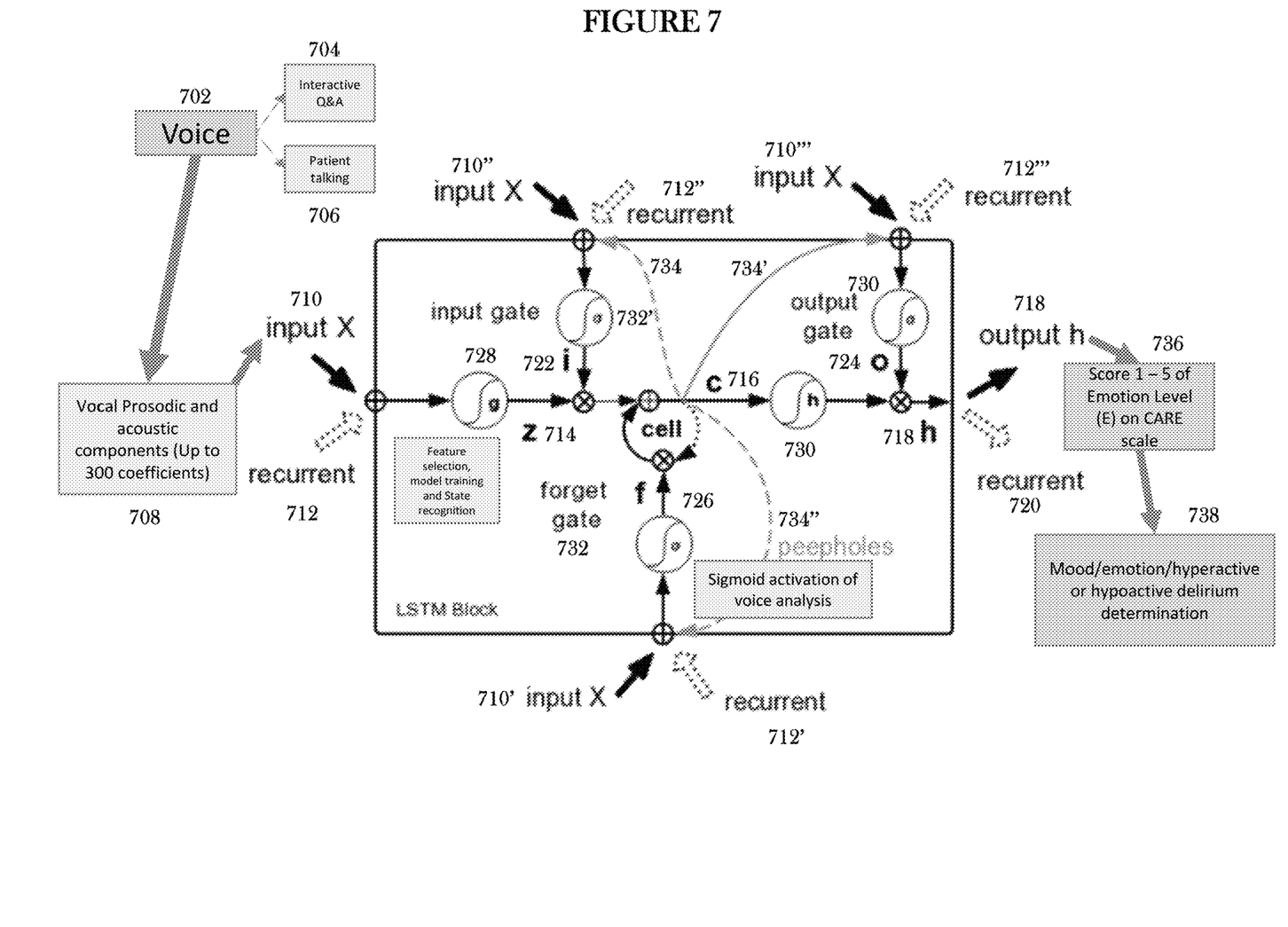
FIG. 7 is a diagram of a basic generic Long Short Term Memory networks (LSTM) showing an input sequence passing through the recurrent neural network of the SeVA system depicting Voice input to an output of "E" component of CARE scale.

FIG. 7 is a diagram of a recurrent neural network used in the system, with an input sequence that is modelled throughout time with a recurrent layer. The diagram shows a high-level recurrent neural network with an input sequence that is modeled throughout time with a recurrent layer that will be used to predict the level of delirium in a patient. In what follows, we show how to adopt the LSTM (as shown in FIG. 7) to predict two CARE Parameters: Emotion and Alertness based on speech, voice and HRV data streams. In the voice analysis, we analyze the vocal parameters 702 that are collected from interactive Q&A 704 as well as the patient's speech 706. That results in a compilation of the acoustic and prosodic features 708 of the voice of the patient, which may be comprised of up to 300 coefficients. This modality can be activated both parallel to the Interactive Automated Q&A 704, or at any other time when the patient is talking 706. We start with the live audio input of the patient and extract statistical features that are in common use in voice processing. We used the OpenSmile feature extraction toolset that is widely used within the affective computing research area (Eyben et al, 2013). Features are signal energy, cepstrum, fundamental frequency (F0), loudness, jitter, Mel-spectra, Mel Frequency Cepstral Coefficients (MFCCs), Perceptual Linear Prediction Cepstral Coefficients (PLPCC), all together around 300 coefficients (AudEERING, 2018). These features are transmitted to SeVA's machine intelligence module for feature selection as input X 710, 710', 710", 710''' model training and state recognition.

Input X 710, 710', 710", 710''' denote the input vector of LSTM network at the current time, the recurrent inputs 712, 712', 712", 712''' from last time step are presented by the dashed arrow. All of the input X 710, 710', 710", 710''' utilize voice 702, interactive Q&A 704, as well as the patient's speech 706 to compile the acoustic and prosodic features 708 of the voice of the patient, as described above. As shown in the diagram, z 714 is the scaled block input, c 716 is the cell state, and h 718 the output of the block along with the recurrent output 720. As shown in the diagram, i 722, o 724, and f 726 are the output value of input gate 728, output gate 730 and forget gate 732, respectively. The neural network is designed to learn when to use short-term and/or long-term patterns. The cell state 716 captures how much to remember from previously learned patterns. The input gate 728 captures the input and for training and building the modules and selects what features to retain in the prediction model. The output gate 730 receive training and output decisions from the system. The forget gate 732 determines how much to forget after each iteration. For example, in certain embodiments, the forget gate will optimally forget 90% of inputs per iteration, or $(0.9)^3$ after three iterations, $(0.9)^{10}$ after ten iterations, and so on. Within the diagram, g(c) 728, h(c) 730, and sigma(c) 732 also indicate input, output and forget sigmoid activation function, respectively. The lines 734, 734', 734" indicate the peephole connections between gates, with the dash lines recurrently connecting back to input gate 728 and forget gate 732, 732', 732" at next time step, and the solid line connecting to output gate 730 at current time step. The peephole connections 734, 734', 734" are used to control the training and output decisions in all aspects of training, filtering, and prediction.

During the training phase, the language of the patient will serve as the time-series. Each word in the sentence is processed sequentially and the objective is to learn the sentiment from the patients' speech. We will characterize the emotional state of the patient based on the CARE's E parameter 736 that will be used to differentiate the type of delirium 738 as Hyperactive or Hypoactive. It can also assist with determining the correct cognitive encouragement approach based on patient's mood.

The LSTM will be trained to quantify the emotional state of the patients into five neuron types: One Neuron is to be used to characterize each emotional level of the patient 736 (CARE emotion score range from 1 to 5). Emotion Level 1 represents the normal voice and 5 represents severe dysarthria (impaired speech).

Figure 8:
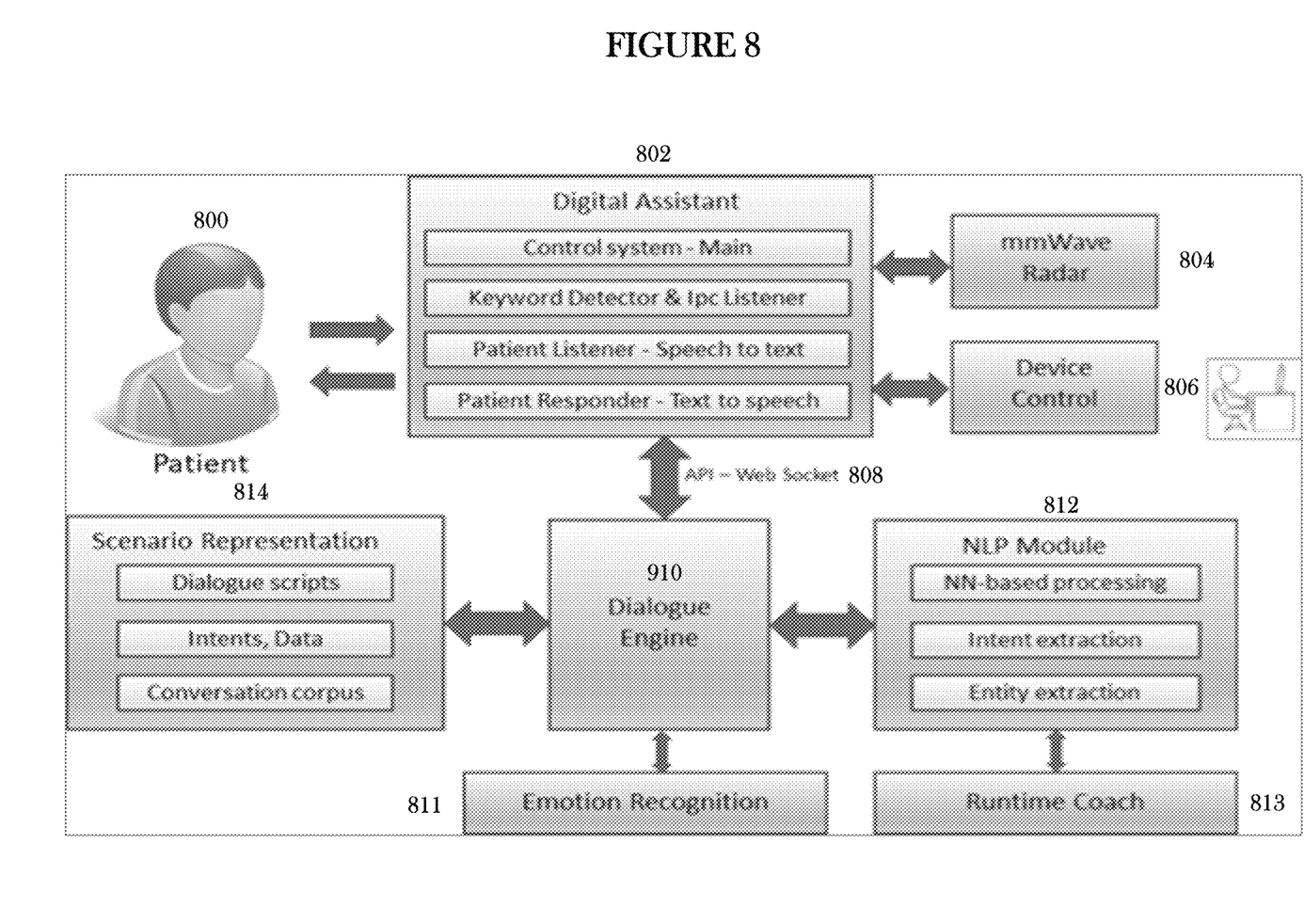
FIG. 8 is a diagram of the exemplary software components of the system.

FIG. 8 is a diagram of the exemplary software components of the system. As shown in the diagram the system is designed to communicate with a patient 802. The patient-facing software is the Digital Assistant 802, which is comprised of the main control system, the keyboard detector and Inter Process Communicator (IPC) listener module, which listens to the patient and converts speech to text, and the patient responder module, which converts text to speech and responds to the patient. The Digital Assistant 802 is connected to the mmWave Radar 804, which predicts movement and behaviors, and the device control module 806, which is responsible for communicating with user devices and the sensors that are connected to the system.

The Digital Assistant 802 uses an Application Programming Interface (API) -Web Socket 808 to connect to the Dialogue Engine 810. The Dialogue Engine 910 is connected to the Scenario Representation module 814 and the Natural Language Processing (NLP) module 912, and the Emotion Recognition Module 811. The NLP module 812 is comprised of the Neural Network (NN)-based processing, intent extraction, and entity extraction functionalities. Intents are the intentions of the end-user, conveyed by the user to the dialogue engine. Entity adds context to the Intent, to enable the Digital Assistant to complete the user request. The NLP module is also connected to the Runtime Coach 813. The Runtime Coach system provides support for further training/tuning the NLP process if necessary. There is a feedback mechanism that allows the assistant to interact with the trainer/coach when a patient is having a hard time understanding or following a conversation. This is similar to having a doctor's assistant faithfully following the doctor's script, yet able to give the doctor feedback in the case the script is not working well. The Scenario Representation module 814 is comprised of Dialogue Scripts, Intents and Conversation Corpus functionalities. It is a descriptive AI tool to represent a set of special codes that capture all the information of patient interactions in different scenarios. It controls all kinds of different conversational scenarios, like checking for delirium, regular patient rounding (checking if patient has problems or needs), patient comfort (playing soft music or telling a prayer), or just some small talk. The Dialogue Scripts Engine runs all conversations with the patient according to the conversation scripts of the Scenario Representation. A medical professional would design these prescriptive scripts and the SeVA assistant will follow them faithfully. Corpus conversion uses words for personality analysis, and from that anticipate questions and responses specific to patient needs. The Dialogue Engine is the central AI part of the SeVA assistant, it orchestrates the conversations according to the scripts, while continuously communicating with other modules.

The foregoing description and drawings should be considered as illustrative only of the principles of the invention. The invention is not intended to be limited by the preferred embodiment and may be implemented in a variety of ways that will be clear to one of ordinary skill in the art. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A digital patient assistance system comprised of:
a server networked to one or more patient computers;
a plurality of sensors connected to said one or more patient computers that transmit patient data to the server, wherein the patient data is comprised of patient gestures, vital signs, and voice data, and wherein the server extracts acoustic features and prosodic features from the voice data and wherein the patient data comprises a training set;
a recurrent neural network trained using the training set to detect signs of delirium and monitor changes in cognition, mood, or emotion in patients using the patient data, wherein the recurrent neural network is further trained to memorize long term and short term patterns in the acoustic features and the prosodic features, and wherein said recurrent neural network outputs recommended actions to a personal computer; and
wherein said recurrent neural network calculates recommended actions based on safety considerations, emotional considerations, and/or a patient's treatment plan.

2. The system of claim 1, wherein the plurality of sensors are one or more of a motion detector, a tv/music entertainment sensor, a smart body sensor, an emotion/stress sensors, and a temperature sensor.

3. The system of claim 1, wherein the patient computers communicate with the server through a portal.

4. The system of claim 1, wherein the server stores patient data in a protected database.

5. The system of claim 1, wherein the personal computer provides a personal chat assistant.

6. The system of claim 1, wherein server identifies patient movements predisposing a patient to falls.

7. The system of claim 6, wherein the server alerts nursing staff when it has identified patient movements predisposing the patient to falls.

8. The system of claim 1, wherein the server determines a patient's emotional, stress, or pain state.

9. The system of claim 1, wherein the server recognizes medical emergencies based on the patient data.

10. A computer-implemented method of patient assistance comprising the steps of:
transmitting patient data received from a plurality of sensors at a patient computer to a server;
receiving patient data at the server, wherein the patient data is comprised of patient gestures, vital signs, and voice data, and wherein the server extracts acoustic features and prosodic features from the voice data; and
training a recurrent neural network to detect signs of delirium and monitor changes in cognition, mood, or emotion in patients using the patient data, wherein the recurrent neural network is further trained to memorize long term and short term patterns in the acoustic features and the prosodic features, and wherein said recurrent neural network outputs recommended actions to a personal computer;
wherein the recurrent neural network calculates recommended actions based on safety considerations, emotional considerations, and/or a patient's treatment plan.

11. The method of claim 10, wherein the plurality of sensors are one or more of a motion detector, a tv/music entertainment sensor, a smart body sensor, an emotion/stress sensors, and a temperature sensor.

12. The method of claim 10, wherein the patient computer communicates with the server through a portal.

13. The method of claim 10, further comprising the step of storing patient data in a protected database.

14. The method of claim 10, further comprising providing a personal chat assistant at the personal computer.

15. The system of claim 10, further comprising identifying patient movements predisposing a patient to falls.

16. The system of claim 15, further comprising alerting nursing staff when it has identified patient movements predisposing the patient to falls.

17. The system of claim 10, further comprising determining a patient's emotional, stress, or pain state.

18. The method of claim 10, further comprising recognizing medical emergencies based on the patient data.

19. A system for detecting patient status comprising:
- a recurrent neural network trained to detect signs of delirium and monitor changes in cognition, mood, or emotion in patients using iteratively received patient data
- wherein the patient data is comprised of patient gestures, vital signs, and voice data, and wherein the iteratively received patient data comprises a training set;
- wherein the recurrent neural network extracts acoustic features and prosodic features from the voice data;
- wherein the recurrent neural network is comprised of an input gate, a forget gate, and an output gate;
- wherein the recurrent neural network is further trained to memorize long term and short term patterns in the acoustic features and the prosodic features;
- wherein the input gate captures patient data and selects a subset of patient to retain;
- wherein the forget gate calculates a percentage of retained patient data for each iteration of training;
- wherein the output gate receives training and output decisions; and
- wherein a plurality of peephole connections between the input gate, the forget gate, and the output gate control training of and output from the recurrent neural network.

20. The system of claim 19, wherein the input gate, the forget gate, and the output gate train the recurrent neural network to recognize short-term and long-term patterns in signs of delirium and changes in cognition, mood, or emotion.

* * * * *